United States Patent
Dodd et al.

(10) Patent No.: US 7,000,963 B2
(45) Date of Patent: Feb. 21, 2006

(54) DISPOSABLE HOLDER FOR USE WITH URINE SPECIMEN CUP

(76) Inventors: Catherine Dodd, 10921 Old Green Bay Rd., Pleasant Prairie, WI (US) 53158; Eric Dodd, 10921 Old Green Bay Rd., Pleasant Prairie, WI (US) 53158

( * ) Notice: Subject to any disclaimer, the term of this patent is extended or adjusted under 35 U.S.C. 154(b) by 35 days.

(21) Appl. No.: 10/436,653

(22) Filed: May 13, 2003

(65) Prior Publication Data

US 2004/0227366 A1   Nov. 18, 2004

(51) Int. Cl.
*B01L 3/00* (2006.01)

(52) U.S. Cl. ............... 294/27.1; 294/31.1; 294/33; 16/425; 220/759; 422/102

(58) Field of Classification Search ......... 294/27.1, 294/28, 30, 31.1, 33, 99.1, 99.2; 16/425; 220/738, 759, 769; 422/102, 104
See application file for complete search history.

(56) References Cited

U.S. PATENT DOCUMENTS

| | | |
|---|---|---|
| 468,710 A | 2/1892 | Mossner |
| 790,411 A | 5/1905 | Watrous |
| 820,577 A | 5/1906 | Johnson |
| 933,442 A | 9/1909 | Hastings |
| 968,956 A | 8/1910 | Key |
| 1,784,112 A | 12/1930 | Rosano |
| 2,074,429 A * | 3/1937 | Randolph .................. 294/33 |
| 2,708,592 A | 5/1955 | Dalkranian |
| 3,232,657 A | 2/1966 | Thompson et al. |
| 5,174,965 A * | 12/1992 | Jones et al. ............... 422/102 |
| 5,492,220 A * | 2/1996 | Estay ........................ 206/363 |
| 5,558,840 A * | 9/1996 | Jones et al. ............... 422/104 |
| 5,788,298 A * | 8/1998 | Cheng ...................... 294/27.1 |
| 6,013,230 A * | 1/2000 | Kuchar ..................... 422/104 |
| 6,039,370 A * | 3/2000 | Dooley et al. ............. 294/1.5 |
| 6,382,459 B1 * | 5/2002 | Liu ............................ 220/769 |
| 6,485,691 B1 * | 11/2002 | Jones ........................ 422/102 |
| 6,719,951 B1 * | 4/2004 | Griffith ..................... 422/102 |

\* cited by examiner

*Primary Examiner*—Dean J. Kramer
(74) *Attorney, Agent, or Firm*—Joseph S. Heino; Patrick M. Bergin

(57) ABSTRACT

A disposable holder for use with urine specimen collection cups has a cup grasping extension incorporated and molded into it. The elongated extension is formed within a recess defined within the overall holder. The holder may be held firmly with one hand and the grasping extension actuated with the other hand. The holder is configured to be held and operated by right and left handed persons. In use, the cup grasping portion of the holder is urged downwardly onto a portion of the perimeter of a cup edge. The specimen is firmly grasped thereby. Upon collection of the specimen, the extension is urged toward the handle so as to open cooperating and opposing cup holding members. In this fashion, the specimen cup and collected specimen are released and the holder is disposed of.

16 Claims, 3 Drawing Sheets

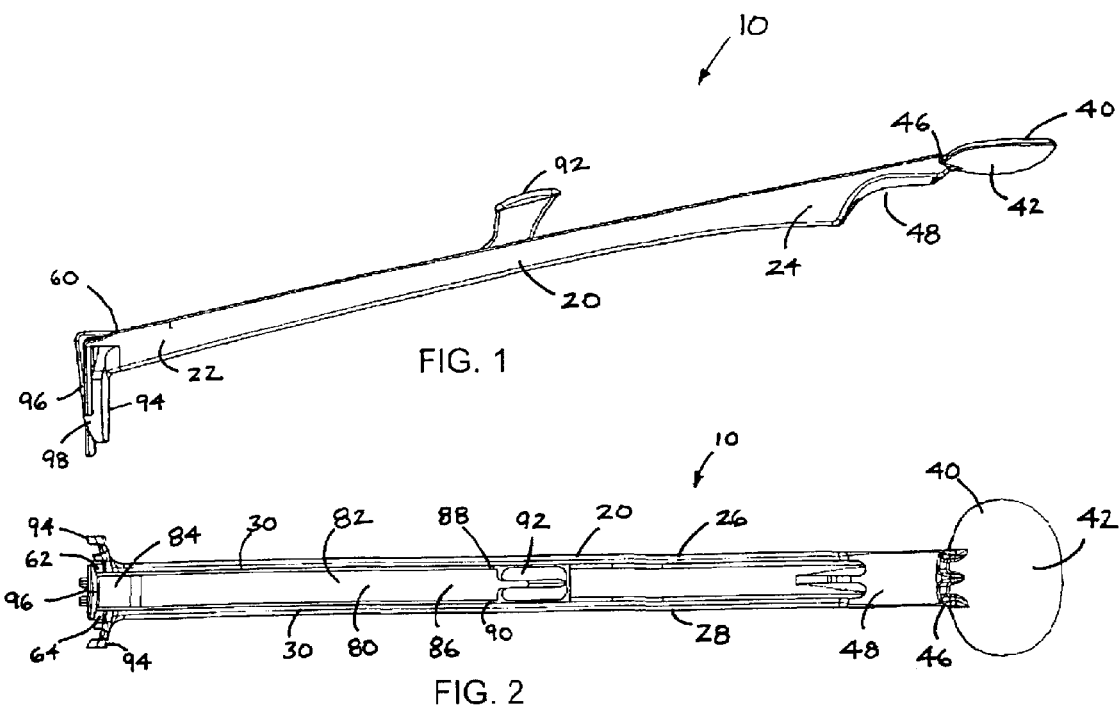

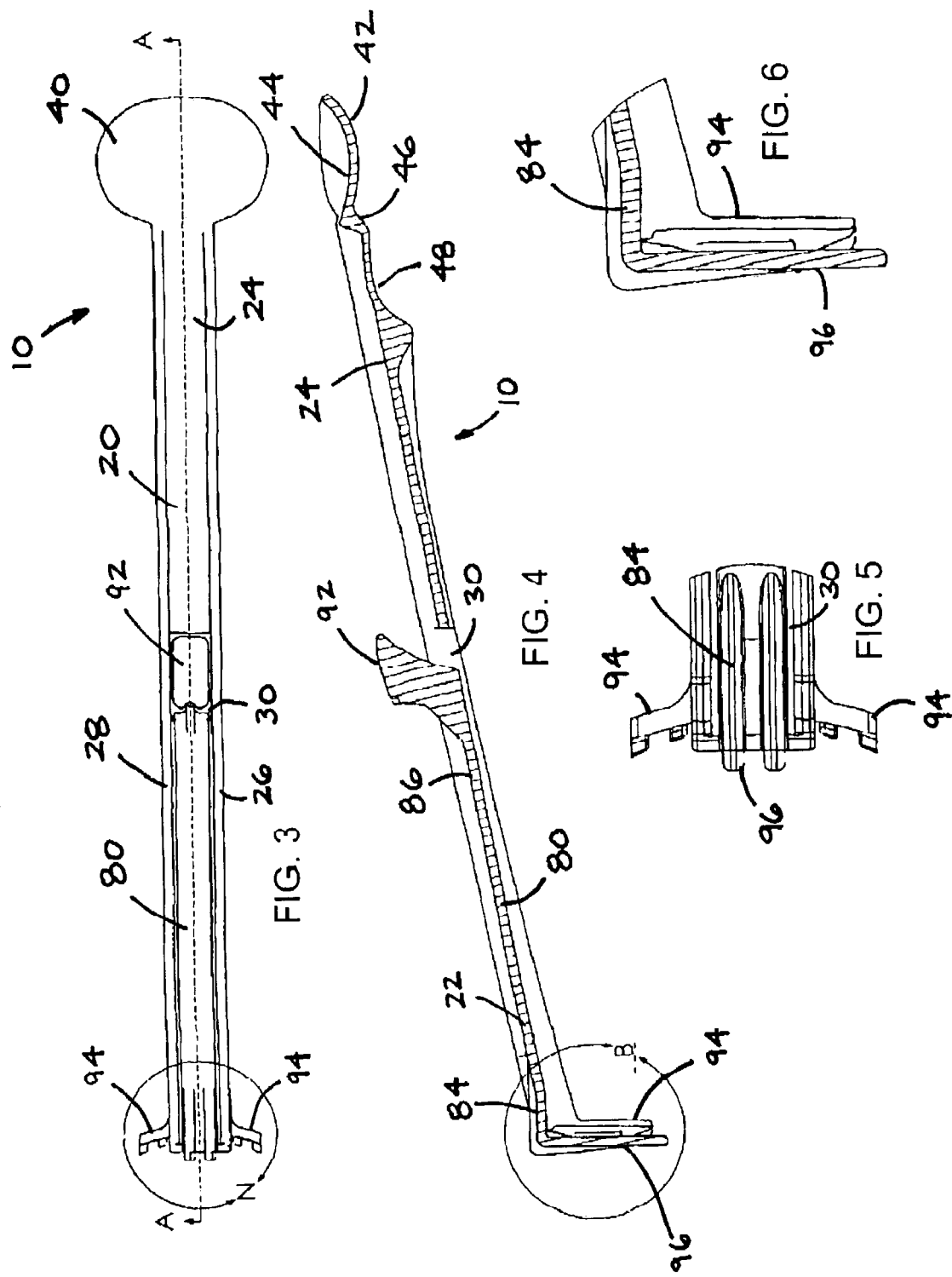

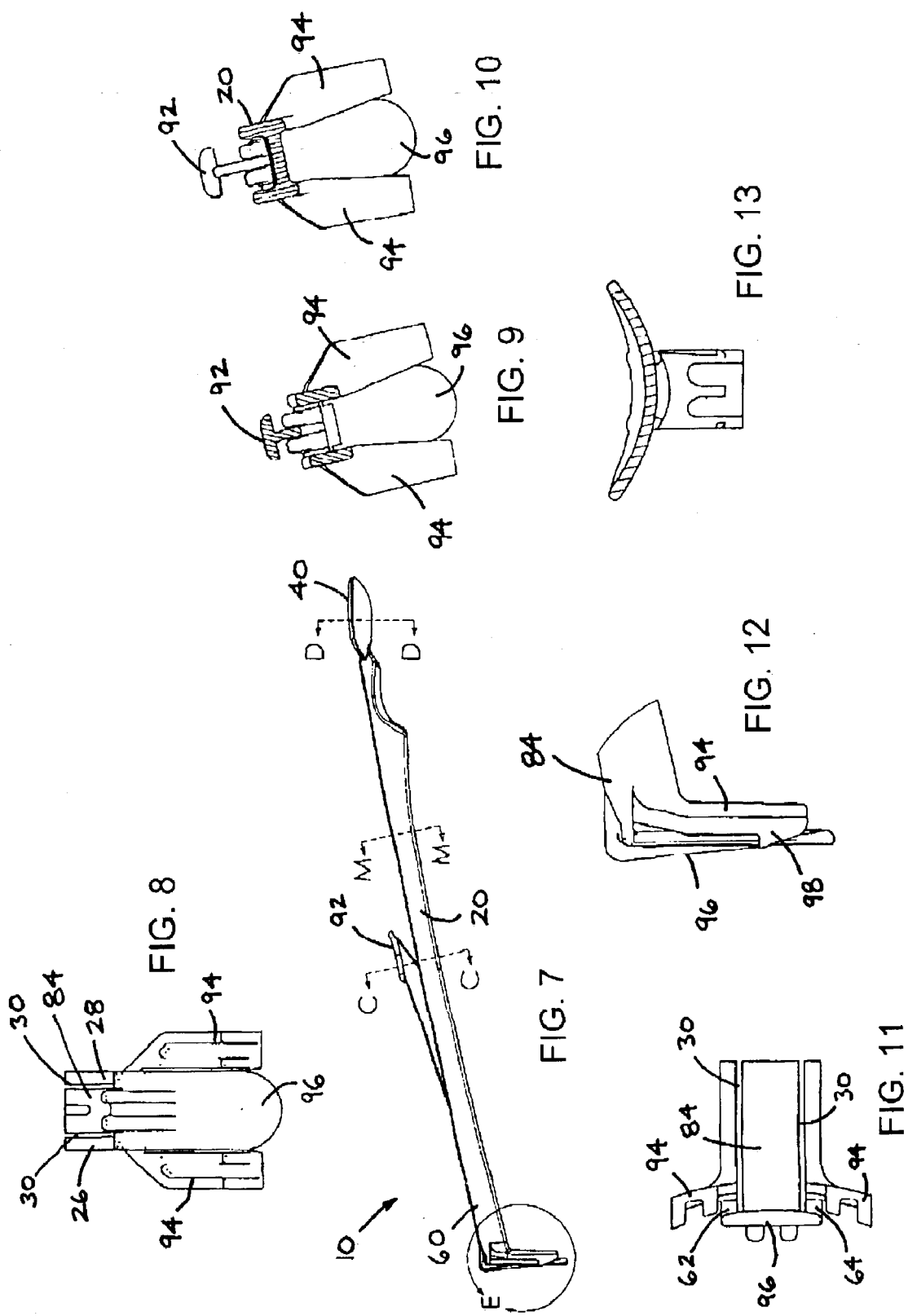

DISPOSABLE HOLDER FOR USE WITH URINE SPECIMEN CUP

FIELD OF THE INVENTION

This invention relates generally to devices that are used in the health care industries. More particularly, it relates to a holder device for use with a standard urine specimen collection cup, which holder is configured to securely hold the cup in a sanitary, sample-taking orientation relative to the patient as the urine specimen is taken. The holder is also configured to allow for the quick release of the cup and specimen contained within it upon completion of specimen collection.

BACKGROUND OF THE INVENTION

The physical, chemical or microscopic analysis of human urine, or urinalysis, is an essential tool in the health care industry. Urinalysis can provide a wide range of information concerning the health and well being of a patient. The examination of urine color and clarity, the measurement of urine acidity and the detection of the presence of protein, sugar, bacteria and other matters found in urine can tell a great deal about the physical condition of the subject patient.

Urinalysis is performed ideally by using a fresh urine specimen, preferably the first voiding of the day since such specimens are the most concentrated and therefore more likely to reveal abnormalities contained within the urine. All urine tests are performed ideally by using clean and uncontaminated collection vessels or containers. Additionally, it is recognized that microscopic urinalysis is best performed within the first one-half hour after collection of the specimen since allowing the sample to stand may cause bacterial overgrowth and even dissolution and dissipation of cellular elements. In short, collection protocol requires that all specimens be collected in sterile containers, then sealed against outside contamination and thereafter refrigerated as soon as possible after collection.

The bacteriological study of urine poses a particular problem due to the inevitable contamination caused by the presence of microorganisms that reside in the vicinity of the human urethral opening. This contamination can be avoided by catheterization of the urinary bladder, but such is obviously an extreme measure and clearly not one recommended for routine examinations. Very reliable bacteriologic urine studies are possible, however, without catheterization by utilizing the so-called "clean-catch mid-stream" technique. For women, collecting a urine specimen in this manner involves partial voiding and then placement of a urinary collection cup between the legs to catch the "mid-stream" urine during continued voiding. This technique is difficult to accomplish without the patient soiling her hands during the urine collection process and without the risk of the patient's hands contacting the collection cup during collection, thus risking inaccurate results due to bacteriologic contamination. In short, eliminating any contact with the urine stream simply provides greater hygiene for the patient and reliability for the health care provider charged with handling and measuring the specimen contained within the cup.

SUMMARY OF THE INVENTION

It is, therefore, a principal object of this invention to provide a new, useful and uncomplicated urine specimen collection cup holder that eliminates the inconveniences, unsanitary practices and ineffective results common with conventional urine collection devices. It is another object of this invention to provide such a cup holder that is manufactured to be disposable. It is still another object of this invention to provide such a cup holder that allows the patient to more easily hold the cup in specimen-collecting relation to her body and minimizes the risk of dropping the cup into the toilet. It is still another object of the present invention to provide such a cup holder that would make urine collection easier and more convenient and make patients feel more at ease with the process, thus reducing the stress associated with medical examinations. It is still another object of the present invention to provide such a cup holder that is particularly beneficial for pregnant or obese women who experience difficulty with reaching around the abdomen to hold a specimen cup. It is another object of the present invention to provide such a cup holder that can provide pediatric assistance for specimen collection from small children. It is still another object of the present invention to provide such a cup holder that minimizes the risk of contamination thereby avoiding the need to repeat the taking of urine samples at a reduced cost to patients and the health care industry in general. It is yet another object of the present invention to provide such a cup holder that allows for the quick attachment to a standard specimen cup and the quick release of the cup following collection of the specimen.

The present invention has obtained these objects. It provides for a disposable holder for use with urine specimen collection cups, the holder having a cup grasping extension incorporated and molded into it. In the preferred embodiment, the elongated extension is formed within a recess defined within the overall holder. The holder may be held firmly with one hand and the grasping extension actuated with the other hand. The holder is configured to be held and operated by right and left handed persons. When ready for use, the cup grasping portion of the holder is urged downwardly onto a portion of the perimeter of a cup edge. The specimen is firmly grasped thereby. Upon collection of the specimen, the extension is urged toward the handle so as to open cooperating and opposing cup holding members. In this fashion, the specimen cup and collected specimen are released and the holder is disposed of.

The foregoing and other features of the urine sample collection cup holder of the present invention will be further apparent from the detailed description which follows.

BRIEF DESCRIPTION OF THE DRAWINGS

FIG. 1 is a right side elevational view of a urine sample collection cup holder constructed in accordance with the present invention.

FIG. 2 is a bottom plan view of the holder shown in FIG. 1.

FIG. 3 is a top plan view of the holder shown in FIG. 1

FIG. 4 is a right side elevational and cross sectioned view of the holder shown in FIG. 1 and taken along line A—A in FIG. 3.

FIG. 5 is an enlarged top plan view of the cup grasping portion that is detailed within line N of FIG. 3.

FIG. 6 is a further enlarged right side and cross sectioned view of the cup grasping portion that is detailed within line B of FIG. 4.

FIG. 7 is a reduced right side elevational view of the holder.

FIG. 8 is an enlarged front elevational view of the holder.

FIG. 9 is an enlarged rear cross sectioned view of the holder taken along line C—C of FIG. 7.

FIG. 10 is an enlarged rear cross sectioned view of the holder taken along line M—M of FIG. 7.

FIG. 11 is an enlarged top plan view of the cup grasping portion of the holder shown in FIG. 7.

FIG. 12 is an enlarged right side elevational view of the cup grasping portion that is detailed within line E of FIG. 7.

FIG. 13 is an enlarged rear cross sectioned view of the handle portion of the holder and taken along line D—D of FIG. 7.

DETAILED DESCRIPTION

Referring now to the drawings in detail, wherein like numerals represent like elements throughout, FIG. 1 illustrates a holder, generally identified 10, that is constructed in accordance with the present invention. The holder 10 is functionally adapted to be used for grasping and then releasing a urine specimen collection cup. As shown in the preferred embodiment, the specimen cup holder 10 includes a longitudinally extending main frame, generally identified 20, having a distal portion, generally identified 40, and a proximal portion, generally identified 60. The distal portion 40 of the frame 20 serves generally as the "handle portion" of the holder 10. The proximal portion 60 of the frame 20 serves generally as the "cup gripping portion" of the holder 10.

The main frame 20 of the holder 10 includes a pair of longitudinally extending side members 26, 28. See FIG. 2. The side members 26, 28 lie generally parallel to one another. At the proximal end 22 of the frame 20 is a longitudinally extending aperture 30 that lays between the side members 26, 28. The proximal end 22 of the frame 20 terminates in the cup gripping portion 60, the detailed construction of which is described below. The main frame 20 also includes a distal end 24 that is integrally formed with the handle portion 40 of the holder 10. As shown, the handle portion 40 includes a somewhat concave member 42 having an upper surface 44. See FIGS. 4 and 13. This upper surface 44 is functionally adapted to receive a user's thumb therewithin, the purpose of which will become further apparent later in this detailed description. The concave member 42 is attached to the distal frame portion 24 by means of a connecting neck 46. Proximal of the neck 46 and lying generally underneath the distal frame portion 24 is a finger recess 48, the purpose of which will also become apparent later in this detailed description.

The aperture 30 defined within the main frame 20 has an extension portion, generally identified 80, formed within it. That is, the extension portion 80 of the holder 10 is integrally formed as part of the holder, and more specifically as part of the main frame 20. The extension portion 80 includes an extension member 82 having a proximal portion 84 and a distal portion 86. To either side of the distal portion 86 is a nominal support member 88, 90. See FIGS. 2 and 3. In the preferred embodiment, the specimen collection cup holder 10 is formed from a polystyrene, polypropylene or polyethylene plastic material which may be injection molded. Accordingly, the main frame 20 and the extension member 82 are integrally formed from a single piece of material. The nominal support members 88, 90 are in the form of mold gates for material flowing between the frame side members 26, 28 and the extension member 82. In the holder 10 of the present invention, the nominal support members 88, 90 are intended to prevent actuation of the device during shipping and handling. When used as intended, the nominal support members 88, 90 essentially break away during use of the holder.

Referring now to FIG. 11, it will be seen that a portion of the distal end 84 of the extension member 82 is integrally formed with the side members 26, 28. That is, the distal end 84 of the extension member 82 and the side members 26, 28 are formed into one conjoined structure at this part of the holder 10. As is specifically shown in FIG. 11, it will be seen that, at the distal end 84 of the extension member, where the distal end 84 becomes an inner cup support 96, a pair of arms 62, 64 is provided to connect that distal end 84 to the side members 26, 28 of the holder 10. The function of the inner cup support 96 will be described in greater detail later in this description. In this fashion, the extension member 82 is actually configured to rotate slightly at this distal end 84. This feature is what this inventor would term a "living hinge." For example, as the lever 92 of the extension member 82 is urged slightly downwardly, the distal end 84 and the arms 62, 64 of the side members 26, 28 actually deform in a "twisting" or torque-like fashion. This twisting is not sufficient to fracture or break the arms 62, 64 or to sever the continuity between the distal end 84 of the extension member 82 and the side members 26, 28, but it is sufficient to provide some resistance when the extension member 82 is urged downwardly. The resilient nature of the plastic material from which the holder 10 is formed allows for this deformation. More importantly, plastic material also possesses the quality of "memory" such that the extension member 82 maintains its original position prior to depression of the extension lever 92. This maintains the various portions of the holder 10 in their original molded position, a position that they tend to want to return to after deformation. The significance of this feature will become apparent later in this detailed description.

As alluded to previously, the proximal cup gripper portion 60 of the holder 10 is really comprised of a number of elements common to the holder portions previously described. For example, a portion of the cup gripper 60 includes the distal end 84 of the extension member 82 and the side members 26, 28. See FIGS. 9 and 10. Additionally, the cup gripper portion 60 also includes a plurality of outer cup support members 94 extending outwardly and downwardly from the side support members 26, 28. Cooperatively opposing the outer cup support members 94 is an inner cup support member 96, as alluded to earlier. See FIGS. 5, 6, 11 and 12. The inner cup support member 96 extends downwardly from the distal end 84 of the extension member 82. As shown in FIG. 11, the arms 62, 64 effectively connect those two structures. The lowermost portion of the outer cup support members 94 includes a hook member 98 which is intended to ensure secure attachment of the holder 10 to the specimen cup, the cup typically including a rim (not shown).

In application, the holder 10 of the present invention could be used to hold one of many commercially available plastic specimen cups, such cups coming in different sizes but generally assuming the same shape. Although the precise size of the cup is not a limitation of the present invention, it would be desirable that the cups used with the holder 10 of the present invention have a top opening that includes a substantially circular rim.

In use, the user would grasp the distal handle portion 40 of the holder 10 with one hand. It should be noted that the holder 10 of the present invention is functionally adapted to be grasped by the left hand or the right hand, thus aiding in the functionality of the device since it need be made in one configuration to serve both right and left handed persons. More specifically, the user would place the thumb of her grasping hand over the concave top 44 of the handle 42, the handle 42 being secured between the thumb and the first finger of that hand. The first or second finger of that same hand would comfortably fit within the recess 48 thereby stabilizing the holder 10 in the grasping hand. Assuming that a cup (not shown) was not already held within the grasping portion 60 of the holder 10, the user would position the rim of the cup below the inner cup support member 96 and the outer cup support members 94 and urge the holder 10 downwardly to the point that the rim of the cup snaps into and is secured by the hook member 98 of the outer cup support members 94. It should be noted here that the preferred embodiment illustrated herein is not the only configuration that would be used to accomplish this intended function. The cup is thereby secured and ready for specimen collection. It should also be noted here that the holder 10 is configured such that it is of sufficient strength to be weight bearing of the collected specimen yet lightweight enough to be disposable. It should also be noted that, during this cup engagement step, the outer and inner cup support members 94, 96 are urged away from each other and the arms 62, 64 are slightly twisted to allow that movement to occur. The plastic memory in the holder 10 allows the cup support members 94, 96 to continue to press a portion of the cup between them. The hook end 98 as previously described ensures that the cup will not slip out from their grasp.

Once collected, the cup is released by the user exerting gentle downward pressure on the lever 92 of the extension member 82. At this point, the nominal support members 88, 90 break away and allow the extension member 82 its full range of movement. As pressure continues to push the lever 92 downwardly, the proximal end 84 of the extension member 82 and the arms 62, 64 are slightly deformed in a "twisting" or torque-like fashion. Although this twisting is not sufficient to fracture or break the continuity between the proximal end 84 of the extension member 82 and the side members 26, 28, it is sufficient to provide some resistance when the extension member 82 is urged downwardly. The resilient nature of the plastic material from which the holder 10 is formed allows for this deformation. It also provides the necessary memory such that the extension member 82 maintains its original position prior to depression of the extension lever 92. As this deformation takes place, the arms 62, 64 are deformed and the inner cup support member 96 extending outwardly and downwardly from the side support members 26, 28 is pushed away from the plurality of outer cup support members 94 so as to release the cup and the specimen contained within it. The holder 10 is then ready for disposal.

From the foregoing detailed description of the illustrative embodiment of the invention set forth herein, it will be apparent that there has been provided a new, useful and uncomplicated urine specimen collection cup holder that eliminates the inconveniences, unsanitary practices and ineffective results common with convention urine collection devices; that is manufactured to be disposable; that allows the patient to more easily hold the cup in specimen-collecting relation to their body and to avoid the risk of dropping the cup into the toilet; that makes urine collection easier and more convenient, allowing patients to feel more at ease with the process thereby reducing the stress associated with medical examinations; that is particularly beneficial for pregnant or obese women who experience difficulty with reaching around the abdomen to hold a specimen cup; and that minimizes the risk of contamination thereby avoiding the need to repeat the taking of urine samples at a reduced costs to patients and the health care industry in general.

What is claimed is:

1. A holder for grasping and releasing a urine specimen cup which comprises
    a main frame, said main frame having a distal portion and a proximal portion,
    a handle integrally formed in the distal frame portion of the main frame,
    a longitudinally-extending aperture defined within the proximal portion of the main frame, the aperture being situated between a pair of opposing and longitudinally-extending side members,
    an extension member disposed within the aperture of the proximal portion of the main frame, said extension member having a distal end and a proximal end, said proximal end being integrally formed as a part of the proximal portion of the main frame, and said extension member being resiliently movable transversely within the aperture and being rotatably movable about its proximal end,
    a specimen cup gripping portion cooperatively and integrally formed in the proximal frame portion and in the proximal end of said extension member,
    wherein a urine specimen cup can be grasped and held within said gripping portion and the urine specimen cup can be released by said gripping portion when the extension member is selectively moved within the main frame aperture.

2. The urine specimen cup holder of claim 1 wherein said main frame side members are disposed generally parallel to one another.

3. The urine specimen cup holder of claim 2 wherein said extension member includes a pair of nominal support members to prevent actuation of the holder during shipping.

4. The urine specimen cup holder of claim 3 wherein said specimen cup gripping portion includes at least one inner cup support member and at least one outer cup support member, the inner and outer cup support members being functionally cooperative with one another to hold the lip of a cup between them.

5. The urine specimen cup holder of claim 4 wherein the proximal portion of said extension member and said specimen cup gripping portion further includes a pair of arms that are integrally formed with and extend between the proximal portion of the extension member and the side members whereby the extension member is movable at said arms relative to said side members.

6. The urine specimen cup holder of claim 5 wherein the proximal portion of said extension member is integrally formed with the at least one inner cup support member.

7. The urine specimen cup holder of claim 6 wherein said extension member includes a distal end having a lever.

8. The urine specimen cup holder of claim 7 wherein said handle includes a concave member for receiving a thumb therewithin and further includes a finger recess defined within said frame whereby the handle can be used to support the cup holder in urine collecting relationship to a user's body.

9. The urine specimen cup holder of claim 8 wherein said main frame, handle and gripping portion are integrally formed from a single piece of molded polystyrene, polypropylene or polyethylene plastic material.

10. A urine specimen cup holder which comprises
    a frame having a distal portion and a proximal portion, said frame including a pair of longitudinally extending side members, said side members being generally parallel to one another, and a longitudinally extending aperture situated between the pair of side members a handle integrally formed in the distal portion of the frame, a gripping portion integrally formed in the proximal portion of the frame, an extension lever means that is integrally formed as part of the frame and movable within the frame for actuating said gripping portion between a closed cup-gripping position and an opened cup-releasing position, wherein said extension lever means includes an extension member integrally formed within the aperture defined between the frame side members, said extension member being movable within the aperture and being resiliently rotatable within it at the proximal portion of the frame, and wherein a urine specimen cup can be grasped and held within said gripping portion when the extension lever means causes said gripping portion to be in the closed position and the urine specimen cup can be released by said gripping portion when the extension lever means causes said gripping portion to be in the opened position.

11. The urine specimen cup holder of claim 10 wherein said gripping portion includes at least one inner cup support member and at least one outer cup support member, the inner and outer cup support members being integrally formed as part of the distal portion of the frame and as part of the extension member and further being functionally cooperative with one another to hold the lip of a cup therebetween.

12. The urine specimen cup holder of claim 11 wherein said extension member includes a proximal portion and said gripping portion further includes a pair of arms that are integrally formed with and extend between the proximal portion of the extension member and the side members whereby the extension member is movable at said arms relative to said side members.

13. The urine specimen cup holder of claim 12 wherein the proximal portion of said extension member is integrally formed with at least one inner cup support member.

14. The urine specimen cup holder of claim 13 wherein said extension member includes a distal end having a lever whereby pressure exerted on the lever moves the extension member relative to the frame.

15. The urine specimen cup holder of claim 14 wherein said handle includes a concave member for receiving a thumb therewithin and further includes a finger recess defined within said frame whereby the handle can be used to support the cup holder in urine collecting relationship to a user's body.

16. The urine specimen cup holder of claim 15 wherein said frame, handle and gripping portion are integrally formed from a single piece of molded polystyrene, polypropylene or polyethylene plastic material.

* * * * *